United States Patent [19]

Marsili

[11] Patent Number: 5,329,001
[45] Date of Patent: Jul. 12, 1994

[54] SUBSTANTIALLY ANHYDROUS CRYSTALLINE CEFADROXIL AND METHOD FOR PRODUCING IT

[75] Inventor: Leonardo Marsili, Segrate, Italy

[73] Assignee: Rifar S.R.L., Milan, Italy

[21] Appl. No.: 825,737

[22] Filed: Jan. 27, 1992

Related U.S. Application Data

[63] Continuation of Ser. No. 427,982, Oct. 30, 1989, abandoned, which is a continuation of Ser. No. 63,870, Jun. 19, 1987, abandoned.

[51] Int. Cl.$^5$ .................. A61K 31/545; C07D 501/22
[52] U.S. Cl. .................... 540/230; 540/228; 540/215
[58] Field of Search .............. 540/230, 228, 215

[56] References Cited

U.S. PATENT DOCUMENTS

| | | | |
|---|---|---|---|
| 4,504,657 | 3/1985 | Bouzard | 544/30 |
| 4,624,948 | 11/1986 | Dünkheim et al. | 540/225 |
| 4,668,782 | 5/1987 | Ichikawa et al. | 540/222 |

FOREIGN PATENT DOCUMENTS

| | | |
|---|---|---|
| 2163514 | 7/1973 | Fed. Rep. of Germany . |
| 2165993 | 8/1973 | France . |
| 2365570 | 4/1978 | France . |

OTHER PUBLICATIONS

Pfeiffer et al., Jour. of Pharmaceutical Sciences vol. 59 No. 12 (1970) pp. 1809–1814.

*Primary Examiner*—Nicholas S. Rizzo
*Attorney, Agent, or Firm*—Oblon, Spivak, McClelland, Maier & Neustadt

[57] ABSTRACT

The invention relates to a substantially anhydrous crystalline cefadroxil having a water content between about 0.8% and 3.9%.

Such cefadroxil is obtained slurrying a cefadroxil solvate of dimethylacetamide, or of N-methyl-2-pyrrolidone or of monomethylformamide, with isopropyl alcohol with up to 4% of water and preferably in the presence of methanol in an amount lower than 60%, at a temperature of about +45° C. to +55° C. and then filtering the so obtained compound.

6 Claims, No Drawings

SUBSTANTIALLY ANHYDROUS CRYSTALLINE CEFADROXIL AND METHOD FOR PRODUCING IT

This application is a continuation of application Ser. No. 07/427,982, filed on Oct. 30, 1989, now abandoned, which is a continuation of application Ser. No. 07/063,870, filed on Jun. 19, 1987, now abandoned.

The present invention relates to a novel crystalline cefadroxil and to a method for producing it.

Cefadroxil is a well known antibiotic substance having antibacterial activity. It is disclosed and claimed in U.S. Pat. No. 3,489,752 according to which it is obtained by acylation of 7-ADCA with an amino-protected derivative of D(−)-alpha-p-hydroxyphenylglycine. U.S. Pat. No. 3,985,741 discloses the preparation of cefadroxil by acylation of 7-ADCA with a mixed anhydride of D-(−)-alpha-p-hydroxyphenylglycine when the latter's alpha-amino group has been blocked with a beta-keto compound such as methyl acetoacetate. The reaction mixture is first added to water and then dimethylformamide is added to the aqueous mixture to precipitate a crystallized solvate of cefadroxil having a $H_2O$ content of more than 3% which, after filtration, is slurried in 90% methanol.

U.S. Pat. No. 4,504,657 describes and claims a different form of cefadroxil, which is the crystalline cefadroxil monohydrate having a well defined X-ray diffraction pattern characterizing said compound. This crystalline cefadroxil monohydrate is obtained (see also the U.S. Pat. No. Re. 31,730) by acylation of silylated 7-ADCA with D(−)-alpha-p-hydroxyphenylglycine chloride hydrochloride. The reaction mixture is added first to water and then dimethylformamide is added to precipitate the dimethylformamide solvate, which, after filtration, is treated in water with a water/solvent mixture to form the solvate. The desired final compound is then precipitated.

The present invention relates to a substantially anhydrous crystalline cefadroxil having a water content from about 0.8% to about 3.9% and having the following X-ray diffraction properties:

| Spacing d(Å) | Relative Intensity |
|---|---|
| 10.42 | 21 |
| 8.54 | 100 |
| 7.06 | 34 |
| 6.38 | 15 |
| 6.05 | 22 |
| 5.84 | 25 |
| 5.12 | 16 |
| 4.79 | 26 |
| 4.58 | 21 |
| 4.35 | 44 |
| 4.26 | 21 |
| 4.18 | 24 |
| 4.02 | 34 |
| 3.90 | 11 |
| 3.78 | 12 |
| 3.52 | 9 |
| 3.46 | 17 |
| 3.27 | 8 |
| 3.18 | 14 |
| 3.12 | 22 |
| 2.93 | 15 |
| 2.89 | 18 |
| 2.82 | 16 |
| 2.61 | 12 |
| 2.55 | 10 |
| 2.52 | 7 |
| 2.35 | 9 |
| 2.30 | 9 |
| 2.18 | 8 |
| 2.13 | 7 |
| 2.08 | 7 |

This substantially anhydrous crystalline cefadroxil is a very stable compound which can be obtained with a very low water content (of about 0.8%): the water content can increase up to about 3.9% when such compound is exposed to a relative humidity lower than 90% without however undergoing any change in its crystalline structure, viz. without changing its X-ray diffraction pattern.

If the above mentioned compound is exposed to a relative humidity higher than 90% for some hours, it can change its crystalline structure to that one of the cefadroxil monohydrate, while increasing its water content above 5%.

The substantially anhydrous crystalline cefadroxil is obtained by adding to an aqueous solution containing cefadroxil just prepared from 7-ADCA a solvent selected from the group consisting of dimethylacetamide, N-methyl-2-pyrrolidone, monomethylformamide, while controlling the pH of the solution within the range of 5.5–6, to give the corresponding cefadroxil solvate which precipitates. The precipitate is filtered off and, after drying of the same, the precipitate is slurried in isopropyl alcohol containing either from about 2% to 4% of water or from about 0.1% to 4% of water and from 0% to about 60% of methanol, at a temperature in the range of about +45° C. to +55° C. The desired cefadroxil is isolated by filtration.

The use of the isopropyl alcohol has proved to be essential. Indeed, if an amount of at least 40% b.v. of isopropyl alcohol is not used, substantially anhydrous cefadroxil is not obtained.

All known methods for transforming the 7-ADCA into an aqueous cefadroxil containing solution can be used. For instance, it is possible to follow the procedure described in Example XVI of the European patent application no. 001,133, or in Examples 1 and 2 of the U.K. patent application no. 2,064,511 or in Examples 1 to 4 of the U.S. Pat. No. 4,234,721.

The invention is illustrated by the following examples in which the NMR spectra were recorded in $D_2O$ solution (15 mg/ml) on a Varian XL-300 spectrometer.

EXAMPLE 1

Cefadroxil Dimethylacetamide Solvate

7-ADCA (45 g) was added to methylene chloride (700 ml) at room temperature. Triethylamine (35.5 g) was added over 15′ with stirring at a temperature below 25° C. Trimethylchlorosilane (43.2 g) was then dropped over a 30′ period. The mixture was stirred at 30° C. for 90′ and then cooled to −10° C.

Dimethylaniline (31 g) and D(−)-p-hydroxyphenylglycyl chloride hydrochloride hemidioxane solvate (63 g) were added and the mixture was stirred at −5° C./0° C. for about 90′. Water (170 ml) was added and the reaction mixture was stirred for 30′. The aqueous phase was diluted with dimethylacetamide (350 ml) and the pH was adjusted to 6.0 by slowly adding diethylamine at 25° C. The mixture was stirred at 20° C. for 120′. The cefadroxil dimethylacetamide solvate was collected by filtration, washed with dimethylacetamide/water 2:1 then with acetone to yield, after drying at 40° C., 81.3 g of the title compound.

K.F.: 0.51%

HPLC Assay: 69.3% on dry basis

PMR: 6.9–7.35 δ(m,C$_6$H$_4$—); 5.59 δ[d, C(7)-H]; 5.15 δ(s,CH—CO); 4.98 δ[d, C$\underline{H}$—S]; 3.02–3.42 δ(m, S—C$\underline{H}_2$); 1.8 δ(s, CH$_3$) characteristic of cefadroxil moiety and the following peaks due to the solvent: 2.88–3.01 δ(s,s, N(CH$_3$)$_2$); 2.04 δ(d,COCH$_3$); $^{13}$C—NMR: 21.07 δ[CH$_3$—C=]; 30.93 δ[CH$_2$—S]; 58.78 δ[CH—NH$_2$]; 59.51 δ[CH—S]; 61.16 δ[NH—CH—CO];

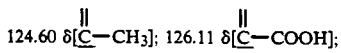
124.60 δ[$\underline{C}$—CH$_3$]; 126.11 δ[$\underline{C}$—COOH];

166.21 δ[CO, β-lactam]; 172.37 δ[COOH]; 172.58 δ[CO—NH]; 129.05 δ, 132.7 δ, 118.99 δ, 160.45 δ[aromatic carbon atoms] characteristic of Cefadroxil moiety and the following peaks due to the solvent: 23.15 δ[CO—CH$_3$]; 37.93 δ[N—CH$_3$]; 40.85 δ[N—CH$_3$]; 176.74 δ[CO].

EXAMPLE 2

Substantially Anhydrous Crystalline Cefadroxil

Cefadroxil dimethylacetamide solvate (50 g) prepared according to Example 1 was slurried at a temperature of 48°–50° C., in isopropyl alcohol (380 ml) having a water content of 3.8%.

After 120' the mixture was cooled to 10° C., filtered and washed with acetone to yield 36.5 g of substantially anhydrous crystalline Cefadroxil having a water content of 2.1%.

HPLC assay: 95.7% on dry basis

The powder exhibits the following X-ray diffraction properties determined with a Diffractometer PW1710 with normal scanning emitting a radiation (wave length: Lambda 1.54051 Angstrom) produced with a Cu/Ni X-ray tube, 40 KV, 40 mA:

| Spacing d(Å) | Relative Intensity |
|---|---|
| 10.42 | 21 |
| 8.54 | 100 |
| 7.06 | 34 |
| 6.38 | 15 |
| 6.05 | 22 |
| 5.84 | 25 |
| 5.12 | 16 |
| 4.79 | 26 |
| 4.58 | 21 |
| 4.35 | 44 |
| 4.26 | 21 |
| 4.18 | 24 |
| 4.02 | 34 |
| 3.90 | 11 |
| 3.78 | 12 |
| 3.52 | 9 |
| 3.46 | 17 |
| 3.27 | 8 |
| 3.18 | 14 |
| 3.12 | 22 |
| 2.93 | 15 |
| 2.89 | 18 |
| 2.82 | 16 |
| 2.61 | 12 |
| 2.55 | 10 |
| 2.52 | 7 |
| 2.35 | 9 |
| 2.30 | 9 |
| 2.18 | 8 |
| 2.13 | 7 |
| 2.08 | 7 |

EXAMPLE 3

Cefadroxil Monomethylformamide Solvate

7-ADCA (30 g) was added to methylene chloride (450 ml), trimethylchlorosilane (28.8 g) was added and the mixture was stirred for 10'. Triethylamine (23.7 g) was then dropped over a 30' period while temperature was allowed to reach 30° C. The mixture was stirred 2 hours at 30° C. and then cooled to −10° C.

Bis-trimethyl-silyl-urea (21 g) and D(−)-p-hydroxyphenylglycyl chloride hydrochloride hemidioxane solvate (45 g) were added and the mixture was allowed to react at −5° C. for 90'. After additional 30' stirring at 0° C., water (115 ml) was added.

The reaction mixture was stirred for 30', the aqueous layer cooled to 5° C. and diluted with monomethylformamide (240 ml). Triethylamine was added slowly over 60' and the pH was adjusted to 5.7 at 20° C. After stirring for 2 hours the slurry was filtered, the filter cake washed with monomethylformamide/water 2:1 and then with acetone to yield, after drying at 40° C., 49 g of the title compound:

K.F.: 0.9%

HPLC Assay: 79.8% on dry basis

PMR: besides the peaks characteristic of Cefadroxil moiety shown in example 1, the following peaks are due to the solvent 7.98 δ[s, HCO]; 2.71 δcis [s, NHCH$_3$]

$^{13}$C—NMR: besides the peaks characteristic of Cefadroxil moiety shown in Example 1, the following peaks are due to the solvent: 27.07 δ[CH$_3$]; 167.6 δ[H—CO].

EXAMPLE 4

Substantially Anhydrous Crystalline Cefadroxil

Cefadroxil monomethylformamide solvate (30 g) prepared according to Example 3 was slurried in 150 ml of a mixture 1:1 of methanol and isopropyl alcohol with 1% of water at 52° C. After 70' at 52° C. the mixture was cooled to 10° C., filtered and washed with acetone to yield 23.5 g of substantially anhydrous crystalline cefadroxil.

K.F.: 1.8%

HPLC Assay: 98.8% on dry basis

The powder exhibits the same X-ray diffraction properties of the product obtained in Example 2.

EXAMPLE 5

Cefadroxil Dimethylacetamide Solvate

Potassium methyl Dane salt of D(−)-p-hydroxyphenylglycine (30.3 g) was added to acetone (170 ml) and the mixture was cooled to −40° C.

Ethylchlorocarbonate (11.15 g) and N-methylmorpholine (0.25 ml) were added at −40° C. The temperature was kept at −35° C. for 120' and then the mixture was cooled to −55° C.

7-ADCA (21.5 g) was charged at +5° C. into water (50 ml) and dimethylsuphoxide (90 ml) and triethylamine (11.3 g) were added. The obtained solution was cooled to 0° C. and the suspension of mixed anhydride (at −55° C.) was added to the solution of 7-ADCA.

The mixture was stirred at −25° C. for 60'; the temperature was raised to 0° C. and HCl 37% was added slowly during 60' to a constant pH 1.8. Methylene chloride (175 ml), was added and the mixture was stirred for 15'. The upper layer was diluted with dimethylacetamide (170 ml) and acetone (70 ml), the pH was adjusted to 6.5 at 0° C. with triethylamine. The mixture was stirred at 0° C. for 2 hours. The solvate was washed with dimethylacetamide/water 2:1 and then with acetone to yield 40.5 g of the title compound after drying at 40° C.

K.F.: 0.63%

HPLC Assay: 69.1% on dry basis

EXAMPLE 6

Cefadroxil 1-Methyl-2-Pyrrolidone Solvate

7-ADCA (30 g) was reacted according to the procedure described in Example 1 using 1-methyl-2-pyrrolidone instead of dimethylacemide. Yield: 52 g

K.F.: 0.85%

HPLC Assay: 68.7% on dry basis

PMR: besides the peaks characteristic of Cefadroxil moiety shown in Example 1, the following peaks are due to the solvent 3.45 $\delta$[t, $CH_2$(5)]; 2.36 $\delta$[t, $CH_2$(3)]; 1.98 $\delta$[q, $CH_2$(4)]; 2.84 $\delta$[s, N—$CH_3$)].

$^{13}C$—NMR: besides the peaks characteristic of Cefadroxil moiety shown in example 1, the following peaks are due to the solvent: 19.71 $\delta$[$CH_2$(4)]; 32.27 $\delta$[N, $CH_3$]; 33.45 $\delta$[$CH_2$(3)]; 52.97 $\delta$[$CH_2$(5)]; 180.84 $\delta$[CO (2)].

EXAMPLE 7

Substantially anhydrous crystalline Cefadroxil

Cefadroxil 1-methyl-2-pyrrolidone solvate (30 g) was slurried in a mixture of 110 ml isopropyl alcohol and 40 ml of methanol with 2.8% of water, kept at 45°–48° C. for 100'. After cooling to 10° C. the mixture was filtered, the product washed with acetone and dried at 40° C.

Yield: 16.5 g of substantially anhydrous cefadroxil

K.F.: 1.8%

HPLC Assay: 97.6% on dry basis

I claim:

1. A crystalline cefadroxyl compound having a water content of from about 0.8% to about 3.9% and having the following X-ray diffraction data:

| Spacing d(A) | Relative Intensity |
| --- | --- |
| 10.42 | 21 |
| 8.54 | 100 |
| 7.06 | 34 |
| 6.38 | 15 |
| 6.05 | 22 |
| 5.84 | 25 |
| 5.12 | 16 |
| 4.79 | 26 |
| 4.58 | 21 |
| 4.35 | 44 |
| 4.26 | 21 |
| 4.18 | 24 |
| 4.02 | 34 |
| 3.90 | 11 |
| 3.78 | 12 |
| 3.52 | 9 |
| 3.46 | 17 |
| 3.27 | 8 |
| 3.18 | 14 |
| 3.12 | 22 |
| 2.93 | 15 |
| 2.89 | 18 |
| 2.82 | 16 |
| 2.61 | 12 |
| 2.55 | 10 |
| 2.52 | 7 |
| 2.35 | 9 |
| 2.30 | 9 |
| 2.18 | 8 |
| 2.13 | 7 |
| 2.08 | 7 |

2. A method of preparing a crystalline cefadroxyl compound having a water content of from about 0.8% to about 3.9%, and having the following x-ray data:

| Spacing d(Å) | Relative Intensity |
| --- | --- |
| 10.42 | 21 |
| 8.54 | 100 |
| 7.06 | 34 |
| 6.38 | 15 |
| 6.05 | 22 |
| 5.84 | 25 |
| 5.12 | 16 |
| 4.79 | 26 |
| 4.58 | 21 |
| 4.35 | 44 |
| 4.26 | 21 |
| 4.18 | 24 |
| 4.02 | 34 |
| 3.90 | 11 |
| 3.78 | 12 |
| 3.52 | 9 |
| 3.46 | 17 |
| 3.27 | 8 |
| 3.18 | 14 |
| 3.12 | 22 |
| 2.93 | 15 |
| 2.89 | 18 |
| 2.82 | 16 |
| 2.61 | 12 |
| 2.55 | 10 |
| 2.52 | 7 |
| 2.35 | 9 |
| 2.30 | 9 |
| 2.18 | 8 |
| 2.13 | 7 |
| 2.08 | 7 | comprising:
a) adding a solvent selected from the group consisting of dimethylacetamide, N-methyl-2-pyrrolidone and monomethylformamide to an aqueous solution of cefadroxyl prepared from 7-ADCA while the pH of the solution is controlled to within the range of 5.5–6 thereby forming a cefadroxyl solvate;
b) precipitating, isolating and drying said cefadroxyl solvate;
c) slurrying said dried cefadroxyl solvate in isopropyl alcohol containing (a) from about 2% to 4% water or (b) from 0.1% to 4% water and from 0% to 60% methanol at a temperature in the range of about +45° C. to +55° C.; and
d) isolating said crystalline cefadroxyl compound.

3. The method of claim 2, wherein in preparing the slurry of said cefadroxil solvate, an amount of isopropyl alcohol of not less than 40% b.v. is used.

4. A slurry mixture comprising dried cefadroxil precipitate and a solvent containing at least 40% b.v. of isopropyl alcohol.

5. The slurry mixture of claim 4, wherein said cefadroxil precipitate is produced by:
a) adding a solvent selected from the group consisting of dimethylacetamide, N-methyl-2-pyrrolidone and monomethylformamide to an aqueous solution of cefadroxil prepared from 7-ADCA while the pH of the solution is controlled to within the range of 5.5–6.0, thereby forming a cefadroxil solvate; and
b) precipitating, isolating and drying said cefadroxil solvate.

6. The slurry mixture of claim 4, wherein said solvent contains, in addition to isopropyl alcohol, from about 2 to 4% water, or from about 0.1 to 4% water and from 0 to about 60% methanol at a temperature in the range of about +45° C. to +55° C.

* * * * *